United States Patent
Chang et al.

(10) Patent No.: US 10,344,287 B2
(45) Date of Patent: Jul. 9, 2019

(54) RECOMBINANT MICROORGANISM PRODUCING QUINOLINIC ACID AND METHOD FOR PRODUCING QUINOLINIC ACID USING SAME

(71) Applicant: CJ CHEILJEDANG CORPORATION, Seoul (KR)

(72) Inventors: Jin Sook Chang, Seoul (KR); Ju Eun Kim, Seoul (KR); So Young Kim, Gwacheon-si (KR); Kwang Ho Na, Seoul (KR); Yong Uk Shin, Yongin-si (KR); Jae Min Lee, Uijeongbu-si (KR); Jae Hee Lee, Seoul (KR); In Kyung Heo, Seoul (KR)

(73) Assignee: CJ CHEILJEDANG CORPORATION, Gyeonggi-Do (KR)

( * ) Notice: Subject to any disclaimer, the term of this patent is extended or adjusted under 35 U.S.C. 154(b) by 53 days.

(21) Appl. No.: 15/323,429

(22) PCT Filed: Jun. 30, 2015

(86) PCT No.: PCT/KR2015/006678
§ 371 (c)(1),
(2) Date: Jan. 2, 2017

(87) PCT Pub. No.: WO2016/006856
PCT Pub. Date: Jan. 14, 2016

(65) Prior Publication Data
US 2017/0159059 A1   Jun. 8, 2017

(30) Foreign Application Priority Data

Jul. 7, 2014   (KR) .................. 10-2014-0084625

(51) Int. Cl.
| | | |
|---|---|---|
| *C12N 1/20* | (2006.01) | |
| *C12N 9/10* | (2006.01) | |
| *C12Q 1/68* | (2018.01) | |
| *C12P 17/12* | (2006.01) | |
| *C07H 21/04* | (2006.01) | |
| *C07H 21/02* | (2006.01) | |
| *C07K 1/00* | (2006.01) | |
| *C12N 15/70* | (2006.01) | |
| *C12N 15/09* | (2006.01) | |
| *C12P 17/10* | (2006.01) | |
| *C12N 9/06* | (2006.01) | |
| *C12N 15/52* | (2006.01) | |

(52) U.S. Cl.
CPC .......... *C12N 15/70* (2013.01); *C12N 9/0022* (2013.01); *C12N 9/1077* (2013.01); *C12N 9/1085* (2013.01); *C12N 15/09* (2013.01); *C12N 15/52* (2013.01); *C12P 17/10* (2013.01); *C12P 17/12* (2013.01); *C12Y 104/03016* (2013.01); *C12Y 204/02019* (2013.01); *C12Y 205/01072* (2013.01)

(58) Field of Classification Search
None
See application file for complete search history.

(56) References Cited

U.S. PATENT DOCUMENTS

2015/0037850 A1   2/2015   Shin et al.

FOREIGN PATENT DOCUMENTS

| KR | 100620092 B1 | 8/2006 |
|---|---|---|
| KR | 1020120082673 A | 7/2012 |
| KR | 1020130080944 A | 7/2013 |
| WO | 2013103246 A2 | 7/2013 |

OTHER PUBLICATIONS

Chandler, et al., De Novo Biosynthesis of Nicotinamide Adenine Dinucleotide in *Escherichia coli*: Excretion of Quinolinic Acid by Mutants Lacking Quinolinate Phosphoribosyl Transferase 1, Journal of Bacteriology, Jul. 1972, vol. 111(1), pp. 98-102.
International Search Report with English Translation for International Application No. PCT/KR2015/006678 dated Sep. 18, 2015.
McLaggan, et al., Analysis of the kefA2 mutation suggests that KefA is a cation-specific channel involved in osmotic adaptation in *Escherichia coli*, Molecular Microbiology (2002) vol. 43(2), pp. 521-536.
Written Opinion for International Application No. PCT/KR2015/006678 dated Sep. 18, 2015.
C. Cui et al., Effect on Mutation of Potassium-Efflux System, KefA, on Mechanosensitive Channels in the Cytoplasmic Membrane of *Escherichia coli*, 1996, pp. 143-152, The Journal of Membrane Biology.
Evert P. Bakker et al., Evidence for Multiple K+ Export Systems in *Escherichia coli*, 1987, pp. 3743-3749, vol. 169, No. 8, Journal of Bacteriology.
Gyorgy Posfai et al., Versatile Insertion Plasmids for Targeted Genome Manipulations in Bacteria: Isolation, Deletion, and Rescue of the Pathogenicity Island LEE of the *Escherichia coli* O157:H7 Genome, 1997, pp. 4426-4428, vol. 179, No. 13, Journal of Bateriology.
Chan Li et al., Identification of mutations that alter the gating of the *Escherichia coli* mechanosensitive channel protein, MscK, 2007, pp. 560-574, 64, 2, Molecular Microbiology, Blackwell Publishing Ltd.
Extended European Search Report for Application No. 15818940.7 dated Nov. 2, 2017.
Japanese Office Action for Application No. 2017500806 dated Dec. 5, 2017.

*Primary Examiner* — Yong D Pak
(74) *Attorney, Agent, or Firm* — Cantor Colburn LLP

(57) ABSTRACT

The present invention relates to a recombinant microorganism producing quinolinic acid, more particularly, a microorganism producing quinolinic acid and having attenuated activity or eliminated activity of a protein having a sequence of SEQ ID NO: 1 and a method of producing quinolinic acid by using the recombinant microorganism.

5 Claims, No Drawings

Specification includes a Sequence Listing.

SEQUENCE LISTING

<160> NUMBER OF SEQ ID NOS: 37

<210> SEQ ID NO 1
<211> LENGTH: 1120
<212> TYPE: PRT
<213> ORGANISM: Escherichia coli K12 W3110

<400> SEQUENCE: 1

```
Met Thr Met Phe Gln Tyr Tyr Lys Arg Ser Arg His Phe Val Phe Ser
1               5                   10                  15

Ala Phe Ile Ala Phe Val Phe Val Leu Leu Cys Gln Asn Thr Ala Phe
            20                  25                  30

Ala Arg Ala Ser Ser Asn Gly Asp Leu Pro Thr Lys Ala Asp Leu Gln
        35                  40                  45

Ala Gln Leu Asp Ser Leu Asn Lys Gln Lys Asp Leu Ser Ala Gln Asp
    50                  55                  60

Lys Leu Val Gln Gln Asp Leu Thr Asp Thr Leu Ala Thr Leu Asp Lys
65                  70                  75                  80

Ile Asp Arg Ile Lys Glu Glu Thr Val Gln Leu Arg Gln Lys Val Ala
                85                  90                  95

Glu Ala Pro Glu Lys Met Arg Gln Ala Thr Ala Ala Leu Thr Ala Leu
            100                 105                 110

Ser Asp Val Asp Asn Asp Glu Glu Thr Arg Lys Ile Leu Ser Thr Leu
        115                 120                 125

Ser Leu Arg Gln Leu Glu Thr Arg Val Ala Gln Ala Leu Asp Asp Leu
    130                 135                 140

Gln Asn Ala Gln Asn Asp Leu Ala Ser Tyr Asn Ser Gln Leu Val Ser
145                 150                 155                 160

Leu Gln Thr Gln Pro Glu Arg Val Gln Asn Ala Met Tyr Asn Ala Ser
                165                 170                 175

Gln Gln Leu Gln Gln Ile Arg Ser Arg Leu Asp Gly Thr Asp Val Gly
            180                 185                 190

Glu Thr Ala Leu Arg Pro Ser Gln Lys Val Leu Met Gln Ala Gln Gln
        195                 200                 205

Ala Leu Leu Asn Ala Glu Ile Asp Gln Gln Arg Lys Ser Leu Glu Gly
    210                 215                 220

Asn Thr Val Leu Gln Asp Thr Leu Gln Lys Gln Arg Asp Tyr Val Thr
225                 230                 235                 240

Ala Asn Ser Ala Arg Leu Glu His Gln Leu Gln Leu Leu Gln Glu Ala
                245                 250                 255

Val Asn Ser Lys Arg Leu Thr Leu Thr Glu Lys Thr Ala Gln Glu Ala
            260                 265                 270

Val Ser Pro Asp Glu Ala Ala Arg Ile Gln Ala Asn Pro Leu Val Lys
        275                 280                 285

Gln Glu Leu Glu Ile Asn Gln Gln Leu Ser Gln Arg Leu Ile Thr Ala
    290                 295                 300

Thr Glu Asn Gly Asn Gln Leu Met Gln Gln Asn Ile Lys Val Lys Asn
305                 310                 315                 320

Trp Leu Glu Arg Ala Leu Gln Ser Glu Arg Asn Ile Lys Glu Gln Ile
                325                 330                 335

Ala Val Leu Lys Gly Ser Leu Leu Leu Ser Arg Ile Leu Tyr Gln Gln
            340                 345                 350

Gln Gln Thr Leu Pro Ser Ala Asp Glu Leu Glu Asn Met Thr Asn Arg
        355                 360                 365

Ile Ala Asp Leu Arg Leu Glu Gln Phe Glu Val Asn Gln Gln Arg Asp
    370                 375                 380

Ala Leu Phe Gln Ser Asp Ala Phe Val Asn Lys Leu Glu Glu Gly His
385                 390                 395                 400

Thr Asn Glu Val Asn Ser Glu Val His Asp Ala Leu Leu Gln Val Val
                405                 410                 415
```

```
Asp Met Arg Arg Glu Leu Leu Asp Gln Leu Asn Lys Gln Leu Gly Asn
                420                 425                 430

Gln Leu Met Met Ala Ile Asn Leu Gln Ile Asn Gln Gln Gln Leu Met
            435                 440                 445

Ser Val Ser Lys Asn Leu Lys Ser Ile Leu Thr Gln Gln Ile Phe Trp
450                 455                 460

Val Asn Ser Asn Arg Pro Met Asp Trp Asp Trp Ile Lys Ala Phe Pro
465                 470                 475                 480

Gln Ser Leu Lys Asp Glu Phe Lys Ser Met Lys Ile Thr Val Asn Trp
                485                 490                 495

Gln Lys Ala Trp Pro Ala Val Phe Ile Ala Phe Leu Ala Gly Leu Pro
            500                 505                 510

Leu Leu Leu Ile Ala Gly Leu Ile His Trp Arg Leu Gly Trp Leu Lys
            515                 520                 525

Ala Tyr Gln Gln Lys Leu Ala Ser Ala Val Gly Ser Leu Arg Asn Asp
        530                 535                 540

Ser Gln Leu Asn Thr Pro Lys Ala Ile Leu Ile Asp Leu Ile Arg Ala
545                 550                 555                 560

Leu Pro Val Cys Leu Ile Ile Leu Ala Val Gly Leu Ile Leu Leu Thr
                565                 570                 575

Met Gln Leu Asn Ile Ser Glu Leu Leu Trp Ser Phe Ser Lys Lys Leu
            580                 585                 590

Ala Ile Phe Trp Leu Val Phe Gly Leu Cys Trp Lys Val Leu Glu Lys
            595                 600                 605

Asn Gly Val Ala Val Arg His Phe Gly Met Pro Glu Gln Gln Thr Ser
            610                 615                 620

His Trp Arg Arg Gln Ile Val Arg Ile Ser Leu Ala Leu Leu Pro Ile
625                 630                 635                 640

His Phe Trp Ser Val Val Ala Glu Leu Ser Pro Leu His Leu Met Asp
                645                 650                 655

Asp Val Leu Gly Gln Ala Met Ile Phe Phe Asn Leu Leu Leu Ile Ala
            660                 665                 670

Phe Leu Val Trp Pro Met Cys Arg Glu Ser Trp Arg Asp Lys Glu Ser
            675                 680                 685

His Thr Met Arg Leu Val Thr Ile Thr Val Leu Ser Ile Ile Pro Ile
690                 695                 700

Ala Leu Met Val Leu Thr Ala Thr Gly Tyr Phe Tyr Thr Thr Leu Arg
705                 710                 715                 720

Leu Ala Gly Arg Trp Ile Glu Thr Val Tyr Leu Val Ile Ile Trp Asn
                725                 730                 735

Leu Leu Tyr Gln Thr Val Leu Arg Gly Leu Ser Val Ala Ala Arg Arg
            740                 745                 750

Ile Ala Trp Arg Arg Ala Leu Ala Arg Arg Gln Asn Leu Val Lys Glu
            755                 760                 765

Gly Ala Glu Gly Ala Glu Pro Pro Glu Glu Pro Thr Ile Ala Leu Glu
770                 775                 780

Gln Val Asn Gln Gln Thr Leu Arg Ile Thr Met Leu Leu Met Phe Ala
785                 790                 795                 800

Leu Phe Gly Val Met Phe Trp Ala Ile Trp Ser Asp Leu Ile Thr Val
                805                 810                 815

Phe Ser Tyr Leu Asp Ser Ile Thr Leu Trp His Tyr Asn Gly Thr Glu
            820                 825                 830
```

Ala Gly Ala Ala Val Val Lys Asn Val Thr Met Gly Ser Leu Leu Phe
                835                 840                 845

Ala Ile Ile Ala Ser Met Val Ala Trp Ala Leu Ile Arg Asn Leu Pro
850                 855                 860

Gly Leu Leu Glu Val Leu Val Leu Ser Arg Leu Asn Met Arg Gln Gly
865                 870                 875                 880

Ala Ser Tyr Ala Ile Thr Thr Ile Leu Asn Tyr Ile Ile Ala Val
                885                 890                 895

Gly Ala Met Thr Val Phe Gly Ser Gly Val Ser Trp Asp Lys Leu
                900                 905                 910

Gln Trp Leu Ala Ala Ala Leu Ser Val Gly Leu Gly Phe Gly Leu Gln
            915                 920                 925

Glu Ile Phe Gly Asn Phe Val Ser Gly Leu Ile Ile Leu Phe Glu Arg
            930                 935                 940

Pro Val Arg Ile Gly Asp Thr Val Thr Ile Gly Ser Phe Ser Gly Thr
945                 950                 955                 960

Val Ser Lys Ile Arg Ile Arg Ala Thr Thr Ile Thr Asp Phe Asp Arg
                965                 970                 975

Lys Glu Val Ile Ile Pro Asn Lys Ala Phe Val Thr Glu Arg Leu Ile
                980                 985                 990

Asn Trp Ser Leu Thr Asp Thr Thr Arg Leu Val Ile Arg Leu Gly
            995                 1000                1005

Val Ala Tyr Gly Ser Asp Leu Glu Lys Val Arg Lys Val Leu Leu
        1010                1015                1020

Lys Ala Ala Thr Glu His Pro Arg Val Met His Glu Pro Met Pro
        1025                1030                1035

Glu Val Phe Phe Thr Ala Phe Gly Ala Ser Thr Leu Asp His Glu
        1040                1045                1050

Leu Arg Leu Tyr Val Arg Glu Leu Arg Asp Arg Ser Arg Thr Val
        1055                1060                1065

Asp Glu Leu Asn Arg Thr Ile Asp Gln Leu Cys Arg Glu Asn Asp
        1070                1075                1080

Ile Asn Ile Ala Phe Asn Gln Leu Glu Val His Leu His Asn Glu
        1085                1090                1095

Lys Gly Asp Glu Val Thr Glu Val Lys Arg Asp Tyr Lys Gly Asp
        1100                1105                1110

Asp Pro Thr Pro Ala Val Gly
        1115                1120

<210> SEQ ID NO 2
<211> LENGTH: 30
<212> TYPE: DNA
<213> ORGANISM: Artificial Sequence
<220> FEATURE:
<223> OTHER INFORMATION: primer for amplification of downstream region
      of kefA

<400> SEQUENCE: 2
gcctgcggat ttaatgacgc gtcgcgcagc                                    30

<210> SEQ ID NO 3
<211> LENGTH: 42
<212> TYPE: DNA
<213> ORGANISM: Artificial Sequence
<220> FEATURE:
<223> OTHER INFORMATION: primer for amplification of downstream region
      of kefA

<400> SEQUENCE: 3
cgaagcagct ccagcctaca cttccggcgc ttcagcgact tt                              42

<210> SEQ ID NO 4
<211> LENGTH: 42
<212> TYPE: DNA
<213> ORGANISM: Artificial Sequence
<220> FEATURE:
<223> OTHER INFORMATION: primer for amplification of FRT-KM

<400> SEQUENCE: 4
aaagtcgctg aagcgccgga agtgtaggct ggagctgctt cg                              42

<210> SEQ ID NO 5
<211> LENGTH: 42
<212> TYPE: DNA
<213> ORGANISM: Artificial Sequence
<220> FEATURE:
<223> OTHER INFORMATION: primer for amplification of FRT-KM

<400> SEQUENCE: 5
ctcagtcgcc gccttcagta aatgggaatt agccatggtc ca                              42

<210> SEQ ID NO 6
<211> LENGTH: 42
<212> TYPE: DNA
<213> ORGANISM: Artificial Sequence
<220> FEATURE:
<223> OTHER INFORMATION: primer for amplification of upstream region of
      kefA

<400> SEQUENCE: 6
tggaccatgg ctaattccca tttactgaag gcggcgactg ag                              42

<210> SEQ ID NO 7
<211> LENGTH: 30
<212> TYPE: DNA
<213> ORGANISM: Artificial Sequence
<220> FEATURE:
<223> OTHER INFORMATION: primer for amplification of upstream region of
      kefA

<400> SEQUENCE: 7
gaaaagaaat taacgcgcga tgatgaggcg                                            30

<210> SEQ ID NO 8
<211> LENGTH: 27
<212> TYPE: DNA
<213> ORGANISM: Artificial Sequence
<220> FEATURE:
<223> OTHER INFORMATION: primer for identifying of kefA deletion

<400> SEQUENCE: 8
ccactctcag tattaagaga gatatta                                               27

<210> SEQ ID NO 9
<211> LENGTH: 28
<212> TYPE: DNA
<213> ORGANISM: Artificial Sequence
<220> FEATURE:
<223> OTHER INFORMATION: primer for identifying of kefA deletion

<400> SEQUENCE: 9
atgtcaaact ggctgtcgat ttgattgt                                              28

<210> SEQ ID NO 10
<211> LENGTH: 3363
<212> TYPE: DNA
<213> ORGANISM: Escherichia coli

<400> SEQUENCE: 10

| | | | | | |
|---|---|---|---|---|---|
| atgactatgt | tccagtatta | caaacgatca | cggcattttg | ttttttcagc | atttattgct | 60 |
| tttgttttg | tcttgttatg | ccagaacacg | gcgtttgcgc | gggcgtcatc | gaatggtgat | 120 |
| ctgccgacaa | aagcggacct | gcaggcgcaa | cttgactcac | taaataaaca | aaaagatctt | 180 |
| tctgctcagg | acaaactggt | gcagcaggat | ctgacagata | cattagccac | cctcgataaa | 240 |
| atcgatcgca | taaagaaga | gacagttcag | ctacggcaaa | aagtcgctga | agcgccggaa | 300 |
| aaaatgcgcc | aggcgaccgc | ggcgttaaca | gcacttagcg | atgtcgataa | cgacgaagaa | 360 |
| acgcgcaaaa | ttctgagcac | gctgtcgttg | cgccagctgg | aaactcgcgt | tgcccaggcg | 420 |
| ctggacgatt | tgcaaaacgc | acaaaacgat | ctggcgtctt | ataacagcca | gctggtttcg | 480 |
| ttacagacgc | agcccgaacg | cgtgcaaaat | gcgatgtata | cgcttcgca | gcagctgcaa | 540 |
| caaattcgca | gtcgtctgga | tgggactgat | gtcggcgaga | cagccttacg | tcccagccag | 600 |
| aaagtgttaa | tgcaggccca | gcaggcgttg | ctgaatgcgg | agattgacca | gcagcgtaaa | 660 |
| agcctggaag | ggaacaccgt | cttgcaggat | accttgcaaa | agcaacgtga | ttacgtgacg | 720 |
| gcgaacagcg | ctcgtctgga | gcaccagtta | caactgttgc | aagaagcggt | aaacagcaag | 780 |
| cgcctgactt | taaccgaaaa | aacggcgcag | gaagccgtct | ccccggatga | agccgcgcgt | 840 |
| attcaggcta | atccgctggt | gaagcaggaa | ctggaaatta | ccagcagtt | aagtcagcgt | 900 |
| ctgattaccg | cgactgaaaa | cggtaatcag | ttgatgcagc | aaaacattaa | agtcaaaaac | 960 |
| tggctggagc | gggcgctgca | atcggaacgc | aatattaaag | agcagattgc | cgtcctgaag | 1020 |
| ggcagcctgc | tgttgtctcg | tatcctttac | cagcaacaac | aaacgctgcc | ctcggcggat | 1080 |
| gaactggaaa | acatgaccaa | ccgcatcgcg | gatttgcgtc | tcgaacagtt | tgaagttaac | 1140 |
| cagcagcgtg | atgcactctt | ccagagcgat | gcgttcgtca | caaactgga | agaaggtcac | 1200 |
| accaacgaag | tcaacagcga | agttcacgat | gcgttattgc | aagtggttga | tatgcgtcgc | 1260 |
| gaattgctgg | atcaactcaa | caaacagttg | ggtaaccagc | tgatgatggc | cattaacctg | 1320 |
| caaatcaacc | agcagcagtt | aatgagtgtg | tcgaaaaacc | tgaaatccat | cctgactcag | 1380 |
| caaatctttt | gggtgaacag | taaccgtcca | atggactggg | actggatcaa | agcgttcccg | 1440 |
| caaagcctga | agatgaatt | taagtcgatg | aaaatcacgg | tgaactggca | aaaagcctgg | 1500 |
| cccgccgttt | ttatcgcttt | cctcgctggt | ttgccgctgc | tgttgattgc | cgggctgatc | 1560 |
| cactggcgtc | tgggctggct | gaaagcgtat | caacaaaaac | tggcttccgc | tgtgggttcc | 1620 |
| ctgcgtaacg | acagccagct | caacacacca | aaagcgatcc | ttatcgacct | gatccgtgcg | 1680 |
| ctgccggtgt | gcctgattat | tctcgcggtt | ggcctgattc | tgttgaccat | gcagctcaac | 1740 |
| atcagcgaac | tgctatggtc | gttcagcaaa | aaactggcga | tattctggct | ggtgtttggc | 1800 |
| ctgtgctgga | aggtactgga | aaaaacggc | gttgccgtac | gtcacttcgg | catgccggaa | 1860 |
| cagcagacca | gccactggcg | tcggcaaatt | gtccgcatca | gtctcgcatt | gctgcctatc | 1920 |
| catttctggt | ctgtggtggc | agaactttcc | ccgctgcatc | tgatggatga | tgtgctgggg | 1980 |
| caagcgatga | ttttcttcaa | cctgctgctg | attgccttcc | tggtatggcc | gatgtgccgc | 2040 |
| gaaagctggc | gtgataaaga | gtcgcacacc | atgcgactgg | tcaccattac | cgtgctgtcg | 2100 |
| ataatcccga | ttgcgctgat | ggtgctgact | gctacaggct | acttctacac | tacgctgcgt | 2160 |

```
ctggcaggac gctggattga aaccgtttat ctggtgatca tctggaacct gctgtaccag      2220
acggtactgc gtggcttaag cgtagcggcg cggcgtatcg cctggcgtcg tgcgctggcg      2280
cgtcggcaga atctggtgaa agagggcgca gaaggtgctg aaccgccgga agaacccacc      2340
attgcactgg agcaagttaa ccagcagacg ctgcgtatta ccatgttgct gatgtttgcg      2400
ctgttcggtg tcatgttctg ggcaatttgg tccgatttga tcaccgtgtt cagctatctc      2460
gacagcatca cgctctggca ttacaacggc actgaagctg cgctgcggt ggtgaaaaac       2520 gtcaccatgg gcagtctgtt gtttgcgatt atcgcctcaa tggtggcctg ggcgttgatt      2580
cgcaacctgc ctggtttact ggaagtgctg gtgctctcgc gactgaatat gcgccagggc      2640
gcgtcgtatg ccattactac catccttaac tacatcatta ttgctgttgg tgcgatgacg      2700
gtgttcggat cgctgggcgt ctcttgggat aaactccagt ggctggccgc agcattatcc      2760
gtaggtcttg gttttggttt acaagaaatt ttcggtaact tcgtctccgg tttgatcatt      2820
ctattcgaac gtccggtgcg tattggcgat acggtaacca ttggtagctt ctcggggacg      2880
gtaagtaaga tccgtattcg tgcgacaacg attaccgatt cgatcgcaa agaagtgatc       2940 atcccgaaca aagcgtttgt taccgagcgt ctgatcaact ggtcgttgac tgacactact      3000
acgcgtctgg tgatccgtct cggcgtggcc tatggctccg atctggaaaa agtgcgtaaa      3060
gtgttactga aggcggcgac tgagcaccca agggtgatgc acgaaccaat gccggaagtc      3120
ttctttacgg catttggtgc cagcacgttg gatcatgagc tgcgtctgta tgtgcgtgaa      3180
ctgcgtgacc gtagtcgtac tgtcgatgag ctgaaccgta ctatcgatca gctgtgccgt      3240
gaaaacgaca tcaacattgc ctttaaccag cttgaagtgc atctgcacaa cgagaagggc      3300
gatgaggtga cggaagtaaa acgcgactac aaaggcgatg acccgacgcc agcggtaggg      3360
taa                                                                    3363

<210> SEQ ID NO 11
<211> LENGTH: 894
<212> TYPE: DNA
<213> ORGANISM: Escherichia coli

<400> SEQUENCE: 11
atgccgcctc gccgctataa ccctgacacc cgacgtgacg agctgctgga acgcattaat       60
ctcgatatcc ccggcgcggt ggcccaggcg ctgcgggaag atttaggcgg aacagtcgat      120
gccaacaatg atattacggc aaaacttttta ccggaaaatt ctcgctctca tgccacggtg      180
atcacccgcg agaatggcgt cttttgcggc aaacgctggg ttgaagaggt gtttattcaa      240
ctggcaggcg acgatgtcac cataatctgg catgtggatg acggcgatgt catcaatgcc      300
aatcaatcct tgttcgaact tgaaggccca tcccgcgtgc tgttaacggg cgaacgcact      360
gcgcttaatt ttgtgcaaac cctttcagga gttgccagta aggtacgcca ctatgtcgaa      420
ttgctggaag caccaacacg cagttgttg gatacgcgca aaaccttacc cggcctgcgt       480
tcagctctga atacgcggt actttgcggc ggcggagcga atcaccgtct ggggctttct      540
gatgccttcc tgatcaaaga aaaccatatt attgcctccg gctcagtgcg ccaggcggtc      600
gaaaaagcgt cctggctgca cccggatgcg ccagtagaag tcgaagtaga gatctggaa       660 gaacttgatg aagccctgaa agcaggagcc gatatcatca tgctggataa cttcgaaaca      720
gaacagatgc gcgaagccgt caaacgcacc aacggcaagg cgctactgga agtgtctggc      780
aacgtcactg acaaaacact gcgtgaattt gccgaaacgg cgtggacttt atctccgtc       840 ggtgcgctaa ctaaacacgt acaagcactc gaccttttcaa tgcgttttcg ctaa          894
```

<210> SEQ ID NO 12
<211> LENGTH: 42
<212> TYPE: DNA
<213> ORGANISM: Artificial Sequence
<220> FEATURE:
<223> OTHER INFORMATION: primer for amplification of downstream region
      of nadC

<400> SEQUENCE: 12
cattatacga acggtacccc cagttgaata aacacctctt ca                    42

<210> SEQ ID NO 13
<211> LENGTH: 18
<212> TYPE: DNA
<213> ORGANISM: Artificial Sequence
<220> FEATURE:
<223> OTHER INFORMATION: primer for amplification of downstream region
      of nadC

<400> SEQUENCE: 13
tggcggcagg ctaatatt                                               18

<210> SEQ ID NO 14
<211> LENGTH: 41
<212> TYPE: DNA
<213> ORGANISM: Artificial Sequence
<220> FEATURE:
<223> OTHER INFORMATION: primer for amplification of loxpCm

<400> SEQUENCE: 14
gttcttccag attctctact tttcgagctc ggtacctacc g                     41

<210> SEQ ID NO 15
<211> LENGTH: 42
<212> TYPE: DNA
<213> ORGANISM: Artificial Sequence
<220> FEATURE:
<223> OTHER INFORMATION: primer for amplification of loxpCm

<400> SEQUENCE: 15
tgaagaggtg tttattcaac tgggggtacc gttcgtataa tg                    42

<210> SEQ ID NO 16
<211> LENGTH: 21
<212> TYPE: DNA
<213> ORGANISM: Artificial Sequence
<220> FEATURE:
<223> OTHER INFORMATION: primer for amplification of upstream region of
      nadC

<400> SEQUENCE: 16
ataaccacca tcagttcgat a                                           21

<210> SEQ ID NO 17
<211> LENGTH: 41
<212> TYPE: DNA
<213> ORGANISM: Artificial Sequence
<220> FEATURE:
<223> OTHER INFORMATION: primer for amplification of upstream region of
      nadC

<400> SEQUENCE: 17
cggtaggtac cgagctcgaa aagtagagaa tctggaagaa c                     41

<210> SEQ ID NO 18
<211> LENGTH: 1551
<212> TYPE: DNA
<213> ORGANISM: Escherichia coli

<400> SEQUENCE: 18

```
ctacgcctgg ctgaccagca tcaggtcatc gttctaagta aaggcccggt aacggaaggt      60
tcaacatttt atgcccaggg cggtattgcc gccgtgtttg atgaaactga cagcattgac     120
tcgcatgtgg aagacacatt gattgccggg gctggtattt gcgatcgcca tgcagttgaa     180
tttgtcgcca gcaatgcacg atcctgtgtg caatggctaa tcgaccaggg ggtgttgttt     240
gatacccaca ttcaaccgaa tggcgaagaa agttaccatc tgacccgtga aggtggacat     300
agtcaccgtc gtattcttca tgccgccgac gccaccggta gagaagtaga aaccacgctg     360
gtgagcaagg cgctgaacca tccgaatatt cgcgtgctgg agcgcagcaa cgcggttgat     420
ctgattgttt ctgacaaaat tggcctgccg gcacgcgac gggttgttgg cgcgtgggta     480
tggaaccgta ataaagaaac ggtggaaacc tgccacgcaa aagcggtggt gctggcaacc     540
ggcggtgcgt cgaaggttta tcagtacacc accaatccgg atatttcttc tggcgatggc     600
attgctatgg cgtggcgcgc aggctgccgg gttgccaatc tcgaatttaa tcagttccac     660
cctaccgcgc tatatcaccc acaggcacgc aatttcctgt aacagaagc actgcgcggc     720 gaaggcgctt atctcaagcg cccggatggt acgcgtttta tgcccgattt tgatgagcgc     780
ggcgaactgg ccccgcgcga tattgtcgcc cgcgccattg accatgaaat gaaacgcctc     840
ggcgcagatt gtatgttcct tgatatcagc cataagcccg ccgatttat tcgccagcat     900 ttcccgatga tttatgaaaa gctgctcggg ctggggattg atctcacaca gaaccggta     960 ccgattgtgc ctgctgcaca ttatacctgc ggtggtgtaa tggttgatga tcatgggcgt    1020
acggacgtcg agggcttgta tgccattggc gaggtgagtt ataccggctt acacggcgct    1080
aaccgcatgg cctcgaattc attgctggag tgtctggtct atggctggtc ggcggcggaa    1140
gatatcacca gacgtatgcc ttatgcccac gacatcagta cgttaccgcc gtgggatgaa    1200
agccgcgttg agaaccctga cgaacgggta gtaattcagc ataactggca cgagctacgt    1260
ctgtttatgt gggattacgt tggcattgtg cgcacaacga agcgcctgga acgcgccctg    1320
cggcggataa ccatgctcca acaagaaata gacgaatatt acgcccattt ccgcgtctca    1380
aataatttgc tggagctgcg taatctggta caggttgccg agttgattgt tcgctgtgca    1440
atgatgcgta aagagagtcg gggggttgcat ttcacgctgg attatccgga actgctcacc    1500
cattccggtc cgtcgatcct ttcccccggc aatcattaca taaacagata a             1551
```

<210> SEQ ID NO 19
<211> LENGTH: 29
<212> TYPE: DNA
<213> ORGANISM: Artificial Sequence
<220> FEATURE:
<223> OTHER INFORMATION: primer for amplification of ORF region of nadB

<400> SEQUENCE: 19

```
aattcatatg aatactctcc ctgaacatt                                        29
```

<210> SEQ ID NO 20
<211> LENGTH: 32
<212> TYPE: DNA
<213> ORGANISM: Artificial Sequence
<220> FEATURE:
<223> OTHER INFORMATION: primer for amplification of ORF region of nadB

<400> SEQUENCE: 20
aattggatcc ctataccact acgcttgatc ac                                32

<210> SEQ ID NO 21
<211> LENGTH: 1044
<212> TYPE: DNA
<213> ORGANISM: Escherichia coli

<400> SEQUENCE: 21
atgagcgtaa tgtttgatcc agacacggcg atttatcctt tcccccgaa gccgacgccg        60
ttaagcattg atgaaaaagc gtattaccgc gagaagataa acgtctgct aaaagaacgt       120
aatgcggtga tggttgccca ctactatacc gatcccgaaa ttcaacaact ggcagaagaa       180
accggtggct gtatttctga ttctctggaa atggcgcgct tcggtgcaaa gcatcccgct       240
tctactttgt tagtcgctgg ggtgagattt atgggagaaa ccgccaaaat tctcagtccg       300
gaaaaaacaa ttctgatgcc gacacttcag gctgaatgtt cactggatct cggctgccct       360
gttgaagaat ttaacgcatt ttgcgatgcc catcccgatc gtactgtcgt cgtctacgcc       420
aacacttctg ctgcggtaaa agcgcgcgca gattgggtgg taacttcaag cattgccgtc       480
gaacttattg atcatcttga tagtttgggt gaaaaatca tctgggcacc cgacaaacat       540
ctggggcgtt acgtgcaaaa acagacgggt ggagacattc tatgctggca gggtgcctgt       600
attgtgcatg atgaatttaa gactcaggcg ttaacccgct tgcaagaaga taccccggat       660
gctgccatac tggtgcatcc agaatcacca caagctattg tcgatatggc ggatgcggtc       720
ggttccacca gtcaactgat cgctgctgcg aaaacattgc cacatcagag gcttattgtg       780
gcaaccgatc ggggtatttt ctacaaaatg cagcaggcgg tgccagataa agagttactg       840
gaagcaccaa ccgcaggtga gggtgcaacc tgccgcagct gcgcgcattg tccgtggatg       900
gccatgaatg gccttcaggc catcgcagag gcattagaac aggaaggaag caatcacgag       960
gttcatgttg atgaaaggct gcgagagagg gcgctggtgc cgctcaatcg tatgctggat       1020
tttgcggcta cactacgtgg ataa                                            1044

<210> SEQ ID NO 22
<211> LENGTH: 31
<212> TYPE: DNA
<213> ORGANISM: Artificial Sequence
<220> FEATURE:
<223> OTHER INFORMATION: primer for amplification of ORF region of nadA

<400> SEQUENCE: 22
aattgggccc atgagcgtaa tgtttgatcc a                                 31

<210> SEQ ID NO 23
<211> LENGTH: 29
<212> TYPE: DNA
<213> ORGANISM: Artificial Sequence
<220> FEATURE:
<223> OTHER INFORMATION: primer for amplification of ORF region of nadA

<400> SEQUENCE: 23
aattgcggcc gctcgtgcct accgcttcg                                    29

<210> SEQ ID NO 24
<211> LENGTH: 294
<212> TYPE: DNA
<213> ORGANISM: Escherichia coli -continued

<400> SEQUENCE: 24

```
ccagcctgtt tacgatgatc ccgctgctta atctgttcat catgcccgtt gccgtttgtg    60
gcgcgacggc gatgtgggtc gattgctatc gcgataaaca cgcgatgtgg cggtaacaat   120
ctaccggtta ttttgtaaac cgtttgtgtg aaacaggggt ggcttatgcc gccccttatt   180
ccatcttgca tgtcattatt tcccttctgt atatagatat gctaaatcct tacttccgca   240
tattctctga gcgggtatgc tacctgttgt atcccaattt catacagtta agga          294
```

<210> SEQ ID NO 25
<211> LENGTH: 25
<212> TYPE: DNA
<213> ORGANISM: Artificial Sequence
<220> FEATURE:
<223> OTHER INFORMATION: primer for amplification of cysK promoter

<400> SEQUENCE: 25

```
ggatccccag cctgtttacg atgat                                          25
```

<210> SEQ ID NO 26
<211> LENGTH: 28
<212> TYPE: DNA
<213> ORGANISM: Artificial Sequence
<220> FEATURE:
<223> OTHER INFORMATION: primer for amplification of cysK promoter

<400> SEQUENCE: 26

```
gggccctcct taactgtatg aaattggg                                       28
```

<210> SEQ ID NO 27
<211> LENGTH: 32
<212> TYPE: DNA
<213> ORGANISM: Artificial Sequence
<220> FEATURE:
<223> OTHER INFORMATION: primer for amplification of pCJ1 promoter

<400> SEQUENCE: 27

```
ccgcggatcc caccgcgggc ttattccatt ac                                  32
```

<210> SEQ ID NO 28
<211> LENGTH: 34
<212> TYPE: DNA
<213> ORGANISM: Artificial Sequence
<220> FEATURE:
<223> OTHER INFORMATION: primer for amplification of pCJ1 promoter

<400> SEQUENCE: 28

```
gatgggccca tcttaatctc ctagattggg tttc                                34
```

<210> SEQ ID NO 29
<211> LENGTH: 297
<212> TYPE: PRT
<213> ORGANISM: Escherichia coli

<400> SEQUENCE: 29

```
Met Pro Pro Arg Arg Tyr Asn Pro Asp Thr Arg Arg Asp Glu Leu Leu
1               5                   10                  15

Glu Arg Ile Asn Leu Asp Ile Pro Gly Ala Val Ala Gln Ala Leu Arg
            20                  25                  30

Glu Asp Leu Gly Gly Thr Val Asp Ala Asn Asn Asp Ile Thr Ala Lys
        35                  40                  45

Leu Leu Pro Glu Asn Ser Arg Ser His Ala Thr Val Ile Thr Arg Glu
    50                  55                  60
```

Asn Gly Val Phe Cys Gly Lys Arg Trp Val Glu Val Phe Ile Gln
 65                  70                  75                  80

Leu Ala Gly Asp Asp Val Thr Ile Ile Trp His Val Asp Asp Gly Asp
                 85                  90                  95

Val Ile Asn Ala Asn Gln Ser Leu Phe Glu Leu Glu Gly Pro Ser Arg
            100                 105                 110

Val Leu Leu Thr Gly Glu Arg Thr Ala Leu Asn Phe Val Gln Thr Leu
        115                 120                 125

Ser Gly Val Ala Ser Lys Val Arg His Tyr Val Glu Leu Leu Glu Gly
    130                 135                 140

Thr Asn Thr Gln Leu Leu Asp Thr Arg Lys Thr Leu Pro Gly Leu Arg
145                 150                 155                 160

Ser Ala Leu Lys Tyr Ala Val Leu Cys Gly Gly Ala Asn His Arg
                165                 170                 175

Leu Gly Leu Ser Asp Ala Phe Leu Ile Lys Glu Asn His Ile Ile Ala
            180                 185                 190

Ser Gly Ser Val Arg Gln Ala Val Glu Lys Ala Ser Trp Leu His Pro
    195                 200                 205

Asp Ala Pro Val Glu Val Glu Val Glu Asn Leu Glu Glu Leu Asp Glu
210                 215                 220

Ala Leu Lys Ala Gly Ala Asp Ile Ile Met Leu Asp Asn Phe Glu Thr
225                 230                 235                 240

Glu Gln Met Arg Glu Ala Val Lys Arg Thr Asn Gly Lys Ala Leu Leu
                245                 250                 255

Glu Val Ser Gly Asn Val Thr Asp Lys Thr Leu Arg Glu Phe Ala Glu
            260                 265                 270

Thr Gly Val Asp Phe Ile Ser Val Gly Ala Leu Thr Lys His Val Gln
        275                 280                 285

Ala Leu Asp Leu Ser Met Arg Phe Arg
    290                 295

<210> SEQ ID NO 30
<211> LENGTH: 540
<212> TYPE: PRT
<213> ORGANISM: Escherichia coli

<400> SEQUENCE: 30

Met Asn Thr Leu Pro Glu His Ser Cys Asp Val Leu Ile Ile Gly Ser
  1               5                  10                  15

Gly Ala Ala Gly Leu Ser Leu Ala Leu Arg Leu Ala Asp Gln His Gln
                 20                  25                  30

Val Ile Val Leu Ser Lys Gly Pro Val Thr Glu Gly Ser Thr Phe Tyr
             35                  40                  45

Ala Gln Gly Gly Ile Ala Ala Val Phe Asp Glu Thr Asp Ser Ile Asp
         50                  55                  60

Ser His Val Glu Asp Thr Leu Ile Ala Gly Ala Gly Ile Cys Asp Arg
 65                  70                  75                  80

His Ala Val Glu Phe Val Ala Ser Asn Ala Arg Ser Cys Val Gln Trp
                 85                  90                  95

Leu Ile Asp Gln Gly Val Leu Phe Asp Thr His Ile Gln Pro Asn Gly
            100                 105                 110

Glu Glu Ser Tyr His Leu Thr Arg Glu Gly Gly His Ser His Arg Arg
        115                 120                 125

```
Ile Leu His Ala Ala Asp Ala Thr Gly Arg Glu Val Glu Thr Thr Leu
130                 135                 140

Val Ser Lys Ala Leu Asn His Pro Asn Ile Arg Val Leu Glu Arg Ser
145                 150                 155                 160

Asn Ala Val Asp Leu Ile Val Ser Asp Lys Ile Gly Leu Pro Gly Thr
                165                 170                 175

Arg Arg Val Val Gly Ala Trp Val Trp Asn Arg Asn Lys Glu Thr Val
                180                 185                 190

Glu Thr Cys His Ala Lys Ala Val Leu Ala Thr Gly Gly Ala Ser
                195                 200                 205

Lys Val Tyr Gln Tyr Thr Thr Asn Pro Asp Ile Ser Ser Gly Asp Gly
210                 215                 220

Ile Ala Met Ala Trp Arg Ala Gly Cys Arg Val Ala Asn Leu Glu Phe
225                 230                 235                 240

Asn Gln Phe His Pro Thr Ala Leu Tyr His Pro Gln Ala Arg Asn Phe
                245                 250                 255

Leu Leu Thr Glu Ala Leu Arg Gly Glu Gly Ala Tyr Leu Lys Arg Pro
                260                 265                 270

Asp Gly Thr Arg Phe Met Pro Asp Phe Asp Glu Arg Gly Glu Leu Ala
                275                 280                 285

Pro Arg Asp Ile Val Ala Arg Ala Ile Asp His Glu Met Lys Arg Leu
290                 295                 300

Gly Ala Asp Cys Met Phe Leu Asp Ile Ser His Lys Pro Ala Asp Phe
305                 310                 315                 320

Ile Arg Gln His Phe Pro Met Ile Tyr Glu Lys Leu Leu Gly Leu Gly
                325                 330                 335

Ile Asp Leu Thr Gln Glu Pro Val Pro Ile Val Pro Ala Ala His Tyr
                340                 345                 350

Thr Cys Gly Gly Val Met Val Asp Asp His Gly Arg Thr Asp Val Glu
                355                 360                 365

Gly Leu Tyr Ala Ile Gly Glu Val Ser Tyr Thr Gly Leu His Gly Ala
370                 375                 380

Asn Arg Met Ala Ser Asn Ser Leu Leu Glu Cys Leu Val Tyr Gly Trp
385                 390                 395                 400

Ser Ala Ala Glu Asp Ile Thr Arg Arg Met Pro Tyr Ala His Asp Ile
                405                 410                 415

Ser Thr Leu Pro Pro Trp Asp Glu Ser Arg Val Glu Asn Pro Asp Glu
                420                 425                 430

Arg Val Val Ile Gln His Asn Trp His Glu Leu Arg Leu Phe Met Trp
                435                 440                 445

Asp Tyr Val Gly Ile Val Arg Thr Thr Lys Arg Leu Glu Arg Ala Leu
450                 455                 460

Arg Arg Ile Thr Met Leu Gln Gln Glu Ile Asp Glu Tyr Tyr Ala His
465                 470                 475                 480

Phe Arg Val Ser Asn Asn Leu Leu Glu Leu Arg Asn Leu Val Gln Val
                485                 490                 495

Ala Glu Leu Ile Val Arg Cys Ala Met Met Arg Lys Ser Arg Gly
                500                 505                 510

Leu His Phe Thr Leu Asp Tyr Pro Glu Leu Leu Thr His Ser Gly Pro
                515                 520                 525

Ser Ile Leu Ser Pro Gly Asn His Tyr Ile Asn Arg
530                 535                 540
```

<210> SEQ ID NO 31
<211> LENGTH: 347
<212> TYPE: PRT
<213> ORGANISM: Escherichia coli

<400> SEQUENCE: 31

Met Ser Val Met Phe Asp Pro Asp Thr Ala Ile Tyr Pro Phe Pro Pro
1               5                   10                  15

Lys Pro Thr Pro Leu Ser Ile Asp Glu Lys Ala Tyr Tyr Arg Glu Lys
            20                  25                  30

Ile Lys Arg Leu Leu Lys Glu Arg Asn Ala Val Met Val Ala His Tyr
        35                  40                  45

Tyr Thr Asp Pro Glu Ile Gln Gln Leu Ala Glu Thr Gly Gly Cys
    50                  55                  60

Ile Ser Asp Ser Leu Glu Met Ala Arg Phe Gly Ala Lys His Pro Ala
65                  70                  75                  80

Ser Thr Leu Leu Val Ala Gly Val Arg Phe Met Gly Glu Thr Ala Lys
                85                  90                  95

Ile Leu Ser Pro Glu Lys Thr Ile Leu Met Pro Thr Leu Gln Ala Glu
            100                 105                 110

Cys Ser Leu Asp Leu Gly Cys Pro Val Glu Glu Phe Asn Ala Phe Cys
        115                 120                 125

Asp Ala His Pro Asp Arg Thr Val Val Tyr Ala Asn Thr Ser Ala
    130                 135                 140

Ala Val Lys Ala Arg Ala Asp Trp Val Val Thr Ser Ser Ile Ala Val
145                 150                 155                 160

Glu Leu Ile Asp His Leu Asp Ser Leu Gly Glu Lys Ile Ile Trp Ala
                165                 170                 175

Pro Asp Lys His Leu Gly Arg Tyr Val Gln Lys Gln Thr Gly Gly Asp
            180                 185                 190

Ile Leu Cys Trp Gln Gly Ala Cys Ile Val His Asp Glu Phe Lys Thr
        195                 200                 205

Gln Ala Leu Thr Arg Leu Gln Glu Glu Tyr Pro Asp Ala Ala Ile Leu
    210                 215                 220

Val His Pro Glu Ser Pro Gln Ala Ile Val Asp Met Ala Asp Ala Val
225                 230                 235                 240

Gly Ser Thr Ser Gln Leu Ile Ala Ala Lys Thr Leu Pro His Gln
                245                 250                 255

Arg Leu Ile Val Ala Thr Asp Arg Gly Ile Phe Tyr Lys Met Gln Gln
            260                 265                 270

Ala Val Pro Asp Lys Glu Leu Leu Glu Ala Pro Thr Ala Gly Glu Gly
        275                 280                 285

Ala Thr Cys Arg Ser Cys Ala His Cys Pro Trp Met Ala Met Asn Gly
    290                 295                 300

Leu Gln Ala Ile Ala Glu Ala Leu Glu Gln Glu Gly Ser Asn His Glu
305                 310                 315                 320

Val His Val Asp Glu Arg Leu Arg Glu Arg Ala Leu Val Pro Leu Asn
                325                 330                 335

Arg Met Leu Asp Phe Ala Ala Thr Leu Arg Gly
            340                 345

<210> SEQ ID NO 32
<211> LENGTH: 21
<212> TYPE: DNA
<213> ORGANISM: Artificial Sequence

```
<220> FEATURE:
<223> OTHER INFORMATION: primer for amplification of kefA ORF with TTG

<400> SEQUENCE: 32
ttgactatgt tccagtatta c                                              21

<210> SEQ ID NO 33
<211> LENGTH: 26
<212> TYPE: DNA
<213> ORGANISM: Artificial Sequence
<220> FEATURE:
<223> OTHER INFORMATION: primer for amplification of kefA ORF with TTG

<400> SEQUENCE: 33
cgcggatccg tgagtcaagt tgcgcc                                         26

<210> SEQ ID NO 34
<211> LENGTH: 29
<212> TYPE: DNA
<213> ORGANISM: Artificial Sequence
<220> FEATURE:
<223> OTHER INFORMATION: primer for amplification of kefA self promoter

<400> SEQUENCE: 34
cgcgagctcc cctgaatctg actccagga                                      29

<210> SEQ ID NO 35
<211> LENGTH: 29
<212> TYPE: DNA
<213> ORGANISM: Artificial Sequence
<220> FEATURE:
<223> OTHER INFORMATION: primer for amplification of kefA self promoter

<400> SEQUENCE: 35
cgcgagctcc cctgaatctg actccagga                                      29

<210> SEQ ID NO 36
<211> LENGTH: 29
<212> TYPE: DNA
<213> ORGANISM: Artificial Sequence
<220> FEATURE:
<223> OTHER INFORMATION: primer for pRhtB kefA

<400> SEQUENCE: 36
ccgatatcat gactatgttc cagtattac                                      29

<210> SEQ ID NO 37
<211> LENGTH: 30
<212> TYPE: DNA
<213> ORGANISM: Artificial Sequence
<220> FEATURE:
<223> OTHER INFORMATION: primer for pRhtB kefA

<400> SEQUENCE: 37
cccaagcttt taccctaccg ctggcgtcgg                                     30
```

US 10,344,287 B2

RECOMBINANT MICROORGANISM PRODUCING QUINOLINIC ACID AND METHOD FOR PRODUCING QUINOLINIC ACID USING SAME

TECHNICAL FIELD

The present inventive concept is related to a recombinant microorganism producing quinolinic acid, and a method of producing quinolinic acid using the recombinant microorganism.

BACKGROUND ART

Quinolinic acid (2,3-pyridine-dicarboxylic acid) has a wide variety of applications as a precursor of chemicals, such as medical and agricultural chemicals, dyes, or the like.

Quinolinic acid can be prepared by chemical or biological synthesis methods. In a chemical manner, quinolinic acid is generally prepared by oxidation of quinoline. In a biological manner, a method of producing quinolinic acid in an *Escherichia coli* (*E. coli*) strain is disclosed, wherein the *E. coli* strain enhances the expression of two enzymes, L-aspartate oxidase (NadB) and quinolinate synthase (NadA), in an *E. coli* of which quinolinate phosphoribosyltransferase (NadC) activity is eliminated.

KefA is a membrane protein belonging to a mechanosensitive (MS) channel present in a microorganism, such as *E. coli*, and has a known function of introducing an ion and a solute into a cell through a cell membrane in a non-specific manner. KefA in *E. coli* constitutes a potassium ($K^+$) efflux system along with KefB and KefC, and more particularly, KefA is known to have an important role in the efflux of $K^+$ upon osmotic down shock (J. Bacteriol. 169, 3743-3749, 1987). In addition, it has been reported that, when a gene of KefA undergoes mutation in *E. coli*, cells become more sensitive to concentrations and pressures of $K^+$, compared to wild-type cells (J. membrane Biol. 150, 143-152). However, as described above, most studies mainly focus on KefA associated with the control of potassium ions in cells, whereas any study on KefA associated with the production of quinolinic acid has not yet been found.

In this regard, the present inventors carried out research about correlation between the modified activity of MS channel proteins and the production of quinolinic acid in high concentrations, thereby completing a method of producing quinolinic acid in high yields.

DETAILED DESCRIPTION OF THE INVENTION

Technical Problem

According to one aspect of the present inventive concept, there is provided a recombinant microorganism producing quinolinic acid, wherein an activity of a protein having a sequence of SEQ ID NO: 1 is attenuated or eliminated.

According to another aspect of the present inventive concept, there is provided a method of producing quinolinic acid by using the recombinant microorganism.

Technical Solution

According to one aspect of the present inventive concept, there is provided a recombinant microorganism producing quinolinic acid, wherein an activity of KefA is attenuated or eliminated.

The term "KefA" as used herein refers to a membrane protein belonging to a mechanosensitive channel, and is also referred to as "MscK". The KefA is depend upon potassium, and may have activity of introducing an ion and a solute into a cell through a cell membrane in a non-specific manner. In particular, the KefA is one example of potassium efflux proteins, and for example, may control the efflux of potassium upon osmotic shock on bacteria.

The KefA may be derived from a microorganism of the genus *Escherichia*. In particular, the KefA may have an amino acid sequence of SEQ ID NO: 1, and non-limiting examples thereof include proteins having an amino acid sequence that has a homology of 80%, more particularly a homology of at least 90%, with the sequence of SEQ ID NO: 1 and substantially having activity of the KefA. In addition, as long as proteins have an amino acid sequence having such a homology above and substantially have the same or corresponding biological activity to the protein having the sequence of SEQ ID NO: 1, it is obvious that proteins having amino acid sequences that partially undergo deletion, modification, substitution, or addition are included in the scope of the present inventive concept.

In addition, a kefA gene sequence may include a polynucleotide sequence encoding the amino acid sequence of SEQ ID NO: 1 or an amino acid sequence having a homology of at least 80% with the amino acid sequence of SEQ ID NO: 1. A polynucleotide encoding the KefA protein may be variously modified in a coding area as long as an amino acid sequence of a protein expressed in the coding area is not changed by degeneracy of a codon or by taking into account a codon that is preferred in an organism in which the protein is to be expressed. The polynucleotide sequence in the kefA gene may be obtained from the genome sequence of *E. coli* (GI:89107872) disclosed in documents or from the database of the National Center for Biotechnology Information (NCBI) and DNA Data Bank of Japan (DDBJ). For example, the polynucleotide sequence in the kefA gene may include a nucleotide sequence of SEQ ID NO: 10 or a nucleotide sequence having a homology of 80%, more particularly a homology of at least 90%, with the sequence of the nucleotide sequence of SEQ ID NO: 10. However, embodiments are not limited thereto.

The term "homology" as used herein refers to a degree of identity between the amino acid sequence or the polynucleotide sequence and a given amino acid sequence or a given polynucleotide sequence, and the homology may be expressed as a percentage. In the present inventive concept, a homologous sequence which is the same as or has similar activity with a given amino acid sequence or a given polynucleotide sequence is represented as "% homology". For example, the homology of sequence may be determined by using the algorithm BLAST according to documents [see Karlin and Altschul, Pro. Natl. Acad. Sci. USA, 90, 5873 (1993)] or FASTA [Pearson, see Methods Enzymol., 183, 63(1990)]. Programs called BLASTN or BLASTX are developed based on the algorithm BLAST, programs [see http://www.ncbi.nlm.nih.gov].

The term "quinolinic acid" as used herein refers to quinolinate or a salt thereof. The term "salt" as used herein refers to a compound prepared by an anion of quinolinic acid and a cation of a base, and examples thereof include a quinolinate sodium salt, a quinolinate potassium salt, a quinolinate ammonium salt, a quinolinate calcium salt, and a quinolinate magnesium salt.

The term "recombinant microorganism" as used herein refers to a microorganism that is naturally or artificially mutated or that is genetically manipulated. A genetically engineered microorganism may be, for example, a microorganism to which an exogenous nucleic acid is introduced according to a genetic engineering method, or a microorganism in which a sequence or a position of an endogenous gene is changed.

The "recombinant microorganism producing quinolinic acid" refers to a microorganism capable of producing and accumulating quinolinic acid by using a carbon source in a medium. In addition, the recombinant microorganism can produce quinolinic acid with high producibility by the attenuation or elimination of the activity of the KefA, compared to a microorganism that is not modified yet. The recombinant microorganism is not limited as long as a microorganism is able to produce and accumulate quinolinic acid, and examples thereof include a microorganism of the genus *Escherichia*, a microorganism of the genus *Enterbacter*, a microorganism of the genus *Erwinia*, a microorganism of the genus *Serratia*, a microorganism of the genus *Providencia*, a microorganism of the genus *Corynebacterium*, and a microorganism of the genus *Brevibacterium*. In detail, the recombinant microorganism may be a microorganism of the genus *Escherichia*. In further detail, the recombinant microorganism may be *E. coli* of the genus *Escherichia*, but is not limited thereto.

The expression "removal of activity or eliminated activity" of an enzyme or a polypeptide as used herein refers to a case where a mentioned protein is not expressed at all in a microorganism or a case where a mentioned protein is expressed in a microorganism but does not have any activity. In addition, the expression "attenuated activity" as used herein refers to a case where activity of a mentioned protein is weakened in a microorganism compared to endogenous activity of the mentioned protein. The term "endogenous activity" as used herein refers to activity of a protein in a natural state, i.e., a protein that is originally included in a microorganism, the protein not undergoing any gene modification.

In detail, the attenuated activity or eliminated activity of the KefA may be resulted by 1) elimination or deletion of genes encoding the KefA protein, 2) modification of regulatory sequences of gene expression to attenuate expression of the genes encoding the KefA protein, or 3) modification of the sequences of the gene on chromosomes to weaken the activity of the KefA or replacement of an endogenous promoter of the gene encoding the KefA protein with a weak promoter, or may be resulted by one or more combinations of the methods above. However, embodiments are not limited thereto.

In further detail, the attenuated activity or eliminated activity of the KefA may be resulted by elimination or deletion of genes encoding the KefA membrane protein. The expression "elimination or deletion of genes" as used herein refers to a case where genes are not expressed, a case where genes are expressed in a small amount, or a case where genes are expressed without having any enzymatic activity. Alternatively, the expression "elimination or deletion of genes" as used herein refers to, to attenuate activity, a part of or all of genes, or a part of or all of regulatory factors in a promoter of genes or a terminator region of genes undergo mutation, substitution, deletion, or insertion to at least one gene. For example, the elimination or the deletion of the genes may be achieved by gene manipulation including homologous recombination, mutation induction, or molecular evolution. When cells include a plurality of the same genes or at least two different polypeptide homologous paralogs, one or two genes may be eliminated or deleted.

In the present inventive concept, in the recombinant microorganism producing quinolinic acid, an activity of quinolinate phosphoribosyltransferase (NadC) may be further attenuated or eliminated.

The term "quinolinate phosphoribosyltransferase" as used herein refers to an enzyme having activity of converting quinolinic acid into nicotinate mononucleotide. When genes having the activity of the quinolinate phosphoribosyltransferase are eliminated, or when expression of genes having the activity of the quinolinate phosphoribosyltransferase is weakened, the production quinolinic acid in cells may be increased.

The quinolinate phosphoribosyltransferase may be derived from a microorganism of the genus *Escherichia*, and more particularly, may have an amino acid sequence of SEQ ID NO: 29. Non-limiting examples of the quinolinate phosphoribosyltransferase include proteins having an amino acid sequence that has a homology of 80%, more particularly a homology of at least 90%, with the amino acid sequence of SEQ ID NO: 29 and substantially having activity of the quinolinate phosphoribosyltransferase. As long as an amino acid has such a homology above and substantially has the same or corresponding biological activity to the protein having the amino acid sequence of SEQ ID NO: 29, it is obvious that proteins having amino acid sequences that partially undergo deletion, modification, substitution, or addition are included in the scope of the present inventive concept.

The nadC gene sequence encoding the quinolinate phosphoribosyltransferase may include a polynucleotide sequence encoding the amino acid sequence of SEQ ID NO: 29. The nadC gene sequence may be obtained from the genome sequence of *E. coli* (GI:89106990) disclosed in the documents or from the database of the NCBI and the DDBJ. In addition, the nadC gene may include a nucleotide sequence of SEQ ID NO: 11 or a nucleotide sequence having a homology of 80%, more particularly a homology of at least 90%, with the sequence of the nucleotide sequence of SEQ ID NO: 11. By attenuation or elimination of the activity of the quinolinate phosphoribosyltransferase, accumulation of the quinolinic acid in cells may be increased.

The expression 'attenuation or elimination of activity' of the quinolinate phosphoribosyltransferase as used herein can be understood by one of ordinary skill in the art in the same manner as in the expression 'attenuation or elimination of activity' of the KefA as described above.

In addition, in the recombinant microorganism producing quinolinic acid, an activity of at least one enzyme selected from the group consisting of L-aspartate oxidase (NadB) and quinolinate synthase (NadA) may be further enhanced. Consequently, accumulation of α-iminosuccinic acid, which is a precursor of the quinolinic acid, and biosynthesis of quinolinic acid from α-iminosuccinic acid may be increased in cells, thereby increasing production of the quinolinic acid.

The term "aspartate oxidase" as used herein refers to an enzyme having activity of oxidizing L-aspartate, and can be named 'L-aspartate oxidase'.

Thus, when activity of L-aspartate oxidase is enhanced, accumulation of iminosuccinic acid, which is a precursor of the quinolinic acid, is increased in cells, thereby increasing production of the quinolinic acid.

The aspartate oxidase may be derived from a microorganism of the genus *Escherichia*. In particular, the aspartate oxidase may have an amino acid sequence of SEQ ID NO: 30, and non-limiting examples thereof include proteins having an amino acid sequence that has a homology of 80%, more particularly a homology of at least 90%, with the amino acid sequence of SEQ ID NO: 30 and substantially having activity of the L-aspartate oxidase. As long as an amino acid has such a homology above and substantially has the same or corresponding biological activity to the protein having the amino acid sequence of SEQ ID NO: 30, it is obvious that proteins having amino acid sequences that partially undergo deletion, modification, substitution, or addition are included in the scope of the present inventive concept.

The nadB gene encoding the aspartate oxidase may include a polynucleotide sequence encoding the amino acid sequence of SEQ ID NO: 30. A sequence of the nadB sequence may be obtained from the genome sequence of *E. coli* (GI:89109380) disclosed in the documents or from the database of the NCBI and the DDBJ. In addition, the nadB gene may include a nucleotide sequence of SEQ ID NO: 18 or a nucleotide sequence having a homology of 80%, more particularly a homology of at least 90%, with the sequence of the nucleotide sequence of SEQ ID NO: 18. However, embodiments are not limited thereto.

The term "quinolinate synthase" as used herein refers to an enzyme having activity of synthesizing quinolinic acid from iminosuccinic acid.

The α-iminosuccinic acid produced upon the activity of the aspartate oxidase speeds up the synthesis of the quinolinic acid through catalysis of the quinolinate synthase, thereby producing the quinolinic acid with further greater producibility. Accordingly, when the expression of genes encoding the quinolinate synthase or the activity of the quinolinate synthase is enhanced, the production of the quinolinic acid may be increased in cells.

The quinolinate synthase may be derived from a microorganism of the genus *Escherichia*. In particular, the quinolinate synthase may have an amino acid sequence of SEQ ID NO: 31, and non-limiting examples thereof include proteins having an amino acid sequence that has a homology of 80%, more particularly a homology of at least 90%, with the amino acid sequence of SEQ ID NO: 31 and substantially having activity of the quinolinate synthase. As long as an amino acid has such a homology above and substantially has the same or corresponding biological activity to the protein having the amino acid sequence of SEQ ID NO: 31, it is obvious that proteins having amino acid sequences that partially undergo deletion, modification, substitution, or addition are included in the scope of the present inventive concept.

The nadA gene encoding the quinolinate synthase may include a polynucleotide sequence encoding the amino acid sequence of SEQ ID NO: 31. A sequence of the nadA sequence may be obtained from the genome sequence of *E. coli* (GI:89107601) disclosed in the documents or from the database of the NCBI and the DDBJ. In addition, the nadA gene encoding the quinolinate synthase may include a nucleotide sequence of SEQ ID NO: 21 or a nucleotide sequence having a homology of 80%, more particularly a homology of at least 90%, with the sequence of the nucleotide sequence of SEQ ID NO: 21. However, embodiments are not limited thereto.

The expression "increased activity" as used herein refers to "enhanced" activity compared to endogenous activity of a mentioned protein. In particular, the increased activity may be achieved by an increase in the copy number of the gene encoding a mentioned protein, modification of regulatory sequences of gene expression so as to increase expression of each of the gene, modification of each of the gene sequence on chromosomes so as to enhance activity of each protein, replacement of an endogenous promoter of the gene with a strong promoter, or any combination thereof. However, embodiments are not limited thereto.

In detail, the increased activity of the aspartate oxidase or the quinolinate synthase may be resulted from transformation using a recombinant vector including polynucleotides encoding such enzymes above. The term "transformation" as used herein refers that a gene is introduced into a host cell so as to expression the gene in a host cell. As long as such a transformed gene can be expressed in a host cell, a gene that is inserted into a chromosome of a host cell or that is positioned outside a chromosome of a host cell can be referred to as the transformed gene. In addition, the transformed gene may include any type of a gene, so long as the gene can be introduced to a host cell and then expressed therein. For example, the transformed gene can be introduced to a host cell in the form of expression cassette, which is a polynucleotide structure and include autonomously all factors required for proper expression. The expression cassette includes a promoter that is typically operably linked to the transformed gene, a transcription termination signal, a ribosome-binding region, and a translation termination signal. The expression cassette may be in the form of an expression vector capable of self-replication. In addition, the transformed gene itself or the transformed gene in the form of a polynucleotide structure may be introduced to a host cell, so as to be operably linked to sequences required for expression in the host cell. The recombinant vector is a means for expressing a protein by introducing DNA into a host cell, and examples thereof include expression vectors known in the art, such as a plasmid vector, a cosmid vector, and a bacteriophage vector. It would have been obvious to one of ordinary skill in the art to prepare such expression vectors according to known methods in the art using the recombinant DNA technology, but embodiments are not limited thereto.

In greater detail, the increased activity of the enzymes above may be resulted from replacement of a promoter operably linked to the gene for a strong promoter. In an embodiment of the present inventive concept, when a promoter operably linked to the nadA gene was replaced with a stronger promoter pCJ1, rather than a promoter pCysK (see KR 10-0620092), it was confirmed that the production of the quinolinic acid was significantly increased (see Table 8). However, embodiments are not limited thereto.

According to another aspect of the present inventive concept, there is provided a method of producing quinolinic acid, the method including: culturing a recombinant microorganism producing the quinolinic acid in a medium; and recovering the quinolinic acid from the medium or the microorganism.

The microorganism producing quinolinic acid is the same as described above.

The culturing of the recombinant microorganism can be performed in an appropriate medium under culture conditions that are known in the art. Such a culturing process may be easily adjusted depending on a microorganism to be selected. The culturing method may include of batch culture, continuous culture, fed-batch culture, or any combination thereof, but embodiments are not limited thereto.

The medium may include various carbon sources, nitrogen sources, and trace elements.

For example, the carbon source may include carbohydrates, such as glucose, sucrose, lactose, fructose, maltose, starch, and cellulose; lipids, such as soybean oil, sunflower oil, castor oil, and coconut oil; fatty acids such as palmitic acid, stearic acid, and linoleic acid; alcohols, such as glycerol and ethanol; organic acids, such as acetic acid, or any combination thereof. For example, the culturing may be performed by using glucose as the carbon source.

The nitrogen source may include an organic nitrogen source, such as peptone, yeast extract, meat extract, malt extract, corn steep liquid (CSL), and soybean meal; an inorganic nitrogen source, such as urea, ammonium sulfate, ammonium chloride, ammonium phosphate, ammonium carbonate, and ammonium nitrate; or any combination thereof.

The medium may include, for example, potassium dihydrogen phosphate, dipotassium phosphate, a sodium-containing salt corresponding thereto, and a metal salt, such as magnesium sulfate or iron sulfate, as phosphorous sources. In addition, the medium may include amino acids, vitamins, and appropriate precursors. The medium or individual components thereof may be added to the culture medium in a batch mode or a continuous mode, but embodiments are not limited thereto.

In addition, in the culturing method, the pH of the culture may be adjusted adding compounds, such as ammonium hydroxide, potassium hydroxide, ammonia, phosphoric acid, or sulfuric acid to the culture in an appropriate manner. In addition, the generation of air bubble may be prevented during the culturing by using an antifoaming agent, such as fatty acid polyglycol ester. To maintain the aerobic condition of the culture, oxygen or oxygen-containing gas (e.g., air) may be injected into the culture. The temperature of the culture may be 20 to 45° C., for example, 22 to 42° C., or 25 to 40° C. The culturing may be continued until the production of the quinolinic acid reaches a desired level, and for example, the culturing may be performed for 10 hours to 160 hours.

Regarding the recovering of the quinolinic acid from the culturing product, the produced quinolinic acid may be collected or recovered from the culturing product by using appropriate methods known in the art associated with the culturing methods in a batch mode, a continuous mode, or a fed-batch mode.

Advantageous Effects of the Invention

The recombinant microorganism, wherein an activity of the protein having the sequence of SEQ ID NO: 1 is attenuated or eliminated, according to one aspect of the present inventive concept can be used for the production of quinolinic acid.

By using the method of producing quinolinic acid according to another aspect of the present inventive concept, the quinolinic acid can be efficiently produced.

MODE OF THE INVENTION

Hereinafter, the present application will be described in more detail with reference to Examples. However, these Examples are for illustrative purposes only, and the scope of the present application is not intended to be limited by these Examples.

Example 1. Preparation of Strain Producing Quinolinic Acid 1-1. Preparation of Quinolinate Phosphoribosyltransferase-Deficient Strain The nadC gene involved in the degradation pathway of quinolinic acid was obtained through PCR using chromosomal DNA of *E. coli* K12 W3110 as a template. The nucleotide sequence information of the nadC gene (NCBI Registration No. "GI:89106990") was obtained from the GeneBank of US National Institute of Health (NIH GenBank). Accordingly, primers of SEQ ID NOs: 12 and 13 to amplify the downstream region of the nadC gene, primers of SEQ ID NOs: 14 and 15 to amplify the upstream and downstream regions of the nadC and loxpCm, and primers of SEQ ID NOs: 16 and 17 to amplify the upstream region of the nadC were synthesized.

PCR was performed using chromosomal DNA of *E. coli* K12 W3110 as a template and oligonucleotides of SEQ ID NOs: 12 and 13, and oligonucleotides of SEQ ID NOs: 16 and 17, as primers to amplify the upstream and downstream regions of the nadC gene of 0.5 kb and 0.3 kb, respectively. In addition, PCR was performed using the pLoxpCat2 plasmid vector including loxpCm as a template, and oligonucleotides of SEQ ID NOs: 14 and 15 as primers to amplify the loxpCm gene having a sequence homologous to the nadC gene at both ends of 1.0 kb. PfuUltra™ DNA polymerase (Stratagene, USA) was used as a polymerase, and PCR was performed by repeating the cycle 30 times including denaturation at 96° C. for 30 seconds, annealing at 53° C. for 30 seconds, and extension at 72° C. for 1 minute.

Afterwards, the nadC-upstream fragment, the nadC-downstream fragment, and the loxpCm fragment obtained from the PCR reactions were used as templates to perform PCR under PCR conditions including 10 cycles including denaturation at 96° C. for 60 seconds, annealing at 50° C. for 60 seconds, and extension at 72° C. for 1 minute and 20 cycles after addition of primers of SEQ ID NOs: 12 and 17. Consequently, a nadC-deficient cassette of 1.8 kb, which contains the upstream region of the nadC gene-loxpCm-downstream region of the nadC gene, was obtained.

*E. coli* K12 W3110 containing pKD46 as a lambda red recombinase expression vector was transformed with the nadC-deficient cassette by means of electroporation, and then, the strain was spread on a Luria-Bertani (LB) plating medium (10 g/L of tryptone, 5 g/L of yeast extract, 10 g/L of NaCl, and 1.5% of agar) containing chloramphenicol as a selective marker, and incubated at 37° C. overnight, to thereby select a strain showing a resistance against chloramphenicol.

The selected strain as a template was directly subjected to PCR using primers of SEQ ID NOs: 13 and 16 under the same conditions, and then, the deletion of the nadC gene was confirmed by identifying the gene size in a wild strain and in the nadC-deficient strain to be 1.6 kb and 1.3 kb, respectively, on the 1.0% agarose gel. Accordingly, the resulting strain was named W3110-ΔnadC.

In addition, the nadC gene was also deleted from the K12 MG1655 strain according to the same method above, and accordingly, the resulting strain was named MG1655-ΔnadC.

1-2. Preparation of KefA-Deficient Strain

The nucleotide sequence of the kefA gene of SEQ ID NO: 10 (NCBI Registration No. "GI::89107872") was obtained from the GenBank. Accordingly, primers of SEQ ID NOs: 2 and 3 to amplify the downstream region of the kefA gene, primers of SEQ ID NOs: 4 and 5 to amplify the upstream and downstream regions of the kefA and FRT-KM, and primers of SEQ ID NOs: 6 and 7 to amplify the upstream region of the kefA were synthesized.

PCR was performed using chromosomal DNA of *E. coli* W3110 as a template, primers of SEQ ID NOs: 2 and 3, and primers of SEQ ID NOs: 6 and 7 to amplify the upstream and downstream regions of the kefA gene of 0.8 Kb and 0.6 Kb, respectively. In addition, PCR was performed using the pKD4 vector including FRT-Km as a template, and oligonucleotides of SEQ ID NOs: 4 and 5 as primers to amplify the FRT-Km gene having a sequence homologous to the kefA gene at both ends of 1.4 Kb. PfuUltra™ DNA polymerase (Stratagene) was used as a polymerase, and PCR was performed by repeating the cycle 30 times including denaturation at 96° C. for 30 seconds, annealing at 53° C. for 30 seconds, and extension at 72° C. for 2 minute. Afterwards, the kefA-upstream fragment, the kefA-downstream fragment, and the FRT-Km fragment obtained from the PCR reactions were used as templates to perform PCR under PCR conditions including 10 cycles including denaturation at 96° C. for 60 seconds, annealing at 50° C. for 60 seconds, and extension at 72° C. for 2 minutes and 20 he cycles after addition of primers of SEQ ID NOs: 6 and 7. Consequently, a kefA-deficient cassette of 2.6 kb, which contains the upstream region of the kefA-FRT-Km-downstream region of the kefA, was obtained.

E. coli W3110-ΔNadC containing pKD46 as a lambda red recombinase expression vector was transformed with the kefA-deficient cassette by means of electroporation, and then, the strain was smeared on a LB plating medium (10 g/L of trypone, 5 g/L of yeast extract, 10 g/L of NaCl, and 1.5% of agar) containing kanamycin as a selective marker, and incubated at 37° C. overnight, to thereby select a strain showing a resistance against kanamycin. The selected strain as a template was directly subjected to PCR using primers of SEQ ID NOs: 8 and 9 under the same conditions, and then, the deletion of the kefA gene was confirmed by identifying the gene size in a wild strain and in the kefA-deficient strain to be 4.2 kb and 1.5 kb, respectively, on the 1.0% agarose gel. Accordingly, the resulting strain was named W3110-ΔnadCΔkefA.

In addition, the kefA gene was also eliminated from the MG1655-ΔnadC strain by using the kefA-deficient cassette according to the same method above, and accordingly, the resulting strain was named MG1655-ΔnadCΔkefA.

1-3. Preparation of Plasmid Expressing L-Aspartate Oxidase in E. coli

The nadB gene encoding wild-type L-aspartate oxidase derived from E. coli was cloned in an expression vector, and the chromosomes of the E. coli K12 W3110 strain (ATCC No 23257) were used as templates. The gene sequence was based on the nucleotide sequence of SEQ ID NO: 18 (NCBI Registration No. "GI:89109380") obtained from the NIH GenBank. The ORF region of the nadB gene was amplified, and primers of SEQ ID NOs: 19 and 20 and having recognition sites of restriction enzymes NdeI and BamHI were synthesized.

PCR was performed using chromosomal DNA of E. coli K12 W3110 as a template and oligonucleotides of SEQ ID NOs: 19 and 20 as primers. PfuUltra™ DNA polymerase (Stratagene, USA) was used as a polymerase, and PCR was performed by repeating the cycle 30 times including denaturation at 96° C. for 30 seconds, annealing at 53° C. for 30 seconds, and extension at 72° C. for 2 minutes. Accordingly, the amplified gene of about 1.9 kb, which contains the nadB ORF gene and the recognition sites of restriction enzymes NdeI and BamHI, was obtained.

The nadB gene obtained through the PCR procedures was recovered through agarose gel elution, and then, was treated with restriction enzymes NdeI and BamHI. Afterwards, the nadB gene was subjected to ligation into a pProLar vector (CloneTech, USA) treated with restriction enzymes NdeI and BamHI, to thereby achieve the expression of L-aspartate oxidase in the nadB gene linked to a pPro promoter. The vector prepared therefrom was named pPro-nadB.

1-4. Preparation of Plasmid Expressing Aspartate Oxidase and Quinolinate Synthase (1) Preparation of pPro-nadB_pCysK-nadA Vector First, the nadA gene encoding quinolinate synthase was obtained through PCR using chromosomal DNA of E. coli W3110 as a template. The nucleotide sequence information of the nadA gene of SEQ ID NO: 21 (NCBI Registration No. "GI:89107601") obtained from the NIH GenBank was used. Then, based on the nadA gene of SEQ ID NO: 21, the ORF region containing from ATG to TAA in the nadA gene was amplified, and primers of SEQ ID NOs: 22 and 23 having the recognition sites of restriction enzymes ApaI and NotI were synthesized.

PCR was performed using chromosomal DNA of E. coli W3110 as a template and oligonucleotides of SEQ ID NOs: 22 and 23 as primers. PfuUltra™ DNA polymerase (Stratagene, USA) was used as a polymerase, and PCR was performed by repeating the cycle 30 times including denaturation at 96° C. for 30 seconds, annealing at 50° C. for 30 seconds, and extension at 72° C. for 2 minutes. Consequently, the amplified gene of about 1.0 kb, which contains the nadA4 gene and the recognition sites of restriction enzymes ApaI and NotI, was obtained.

In addition, a cysK promoter was obtained through PCR procedures using chromosomal DNA of E. coli W3110 as a template. On the nucleotide sequence information (SEQ ID NO: 24) of the promoter located within upstream 0.3 kb of the cysK gene obtained from the NIH GenBank, primers of SEQ ID NOs: 25 and 26 having the recognition sites of restriction enzymes BamHI and ApaI were synthesized so as to ligate the cysK promoter with the amplified nadA gene.

PCR was performed using chromosomal DNA of E. coli W3110 as a template and oligonucleotides of SEQ ID NOs: 25 and 26 as primers. PfuUltra™ DNA polymerase (Stratagene) was used as a polymerase, and PCR was performed by repeating the cycle 30 times including denaturation at 96° C. for 30 seconds, annealing at 50° C. for 30 seconds, and extension at 72° C. for 1 minute. Consequently, the amplified gene of about 0.3 kb, which contains the cysK promoter and restriction enzymes BamHI and ApaI, was obtained.

The nadA gene obtained through PCR procedures was treated with restriction enzymes ApaI and NotI, and the amplified cysK promoter fragment was treated with ApaI and BamHI. The nadA and the cysK promoter fragments that were treated with restriction enzymes were cloned by ligating into the pPro-nadB vector of Example 1-2 treated with restriction enzymes NotI and BamHI, thereby preparing a pPro-nadB_pCysK-nadA vector of 5.9 kb in which the nadB gene and the nadA gene were cloned, wherein the expression of the nadB gene was controlled under a pPro promoter as a constitutive promoter and the expression of the nadA gene was controlled under a promoter of the cysK gene.

(2) Preparation of pPro-nadB_pCJ1-nadA Vector

In order to further enhance the expression of the nadA gene encoding the quinolinate synthase at the end of the biosynthesis process of the quinolinic acid, a strong promoter in K12 W3110, a pCJ1 promoter, instead of the pCysK promoter was used. According to KR 2006-0068505A, the pCJ1 promoter was obtained through PCR using DNA of a plasmid including the pCJ1 promoter as a template. To ligate the pCJ1 promoter with the amplified nadA gene, primers of SEQ ID NOs: 27 and 28 having the recognition sites of restriction enzymes BamHI and ApaI were synthesized.

PCR was performed using chromosomal DNA of E. coli W3110 as a template and oligonucleotides of SEQ ID NOs: 27 and 28 as primers. PfuUltra™ DNA polymerase (Stratagene) was used as a polymerase, and PCR was performed by repeating the cycle 30 times including denaturation at 96° C. for 30 seconds, annealing at 50° C. for 30 seconds, and extension at 72° C. for 1 minute. Consequently, the amplified gene of about 0.3 kb, which contains the pCJ1 promoter and restriction enzymes BamHI and ApaI, was obtained.

The nadA gene obtained through PCR procedures were treated with restriction enzymes ApaI and NotI, and the amplified pCJ1 promoter fragment was treated with ApaI and BamHI. The nadA and the pCJ1 promoter fragments that were treated with the restriction enzymes above were cloned by ligating into the pPro-nadB vector of Example 1-2 treated with restriction enzymes NotI and BamHI, thereby preparing a pPro-nadB_pCJ1-nadA recombinant vector of 5.9 kb in which the nadB gene and the nadA gene were cloned, wherein the expression of the nadB gene was controlled under a pPro promoter as a constitutive promoter and the expression of the nadA gene was controlled under a promoter of the pCJ1 gene.

Example 2. Evaluation of Producibility of Strain Producing Quinolinic Acid 2-1. Titer-Based Confirmation to Compare Producibility of Strain Producing Quinolinic Acid To evaluate the producibility of the quinolinic acid, the plasmid including enhanced nadB and nadA was introduced to each of the W3110-ΔnadC and the MG1655-ΔnadC strains. Regarding the introduction method, the strains were transformed through a CaCl$_2$ method, smeared on a LB-Km plating medium (10 g/L of yeast extract, 5 g/L of NaCl, 10 g/L of tryptone, 1.5% of agar, and 50 ug/L of kanamycin), and then, incubated at 37° C. overnight. Afterwards, a single kanamycin-resistant colony was collected, inoculated in 25 mL of quinolinic acid titer medium by 1 platinum loop, and then, incubated with 250 rpm at 33° C. for 24 to 72 hours. Table 1 below shows the composition of the production medium for the quinolinic acid.

TABLE 1

The composition of titer medium in quinolinic acid flask

| Composition | Concentration (per liter) |
| --- | --- |
| Glucose | 70 g |
| Ammonium sulfate | 17 g |
| KH$_2$PO$_4$ | 1.0 g |
| MgSO$_4$•7H$_2$O | 0.5 g |
| FeSO$_4$•7H$_2$O | 5 mg |
| MnSO$_4$•8HO | 5 mg |
| ZnSO$_4$ | 5 mg |
| Calcium carbonate | 30 g |
| Yeast extract | 2 g |
| Methionine | 0.15 g |

The quinolinic acid in the culture broth was analyzed by HPLC, and the results are shown in Table 2 below. That is, the results indicate the ability of the strain to produce the quinolinic acid. As shown in Table 2, depending on the extent of the expression of the quinolinic acid base strain and the expression of the nadBA, differences in the production of the quinolinic acid were observed. In particular, when the expression of the nadA gene was enhanced by using the pCJ1 promoter, which has a stronger expression strength than that of the pCysK promoter, it was confirmed that the production of the quinolinic acid was significantly increased in the wild-type *E. coli* K12 strains W3110-ΔnadC and MG1655-ΔnadC.

TABLE 2

| Base strain | Plasmid | Quinolinic acid (g/L) |
| --- | --- | --- |
| W3110-ΔnadC | pPro-nadB_pCysK-nadA | 0.5 |
| MG1655-ΔnadC | | 0.3 |
| W3110-ΔnadC | pPro-nadB_pCJ1-nadA | 3.8 |
| MG1655-ΔnadC | | 2.0 |

2-2. Evaluation of Quinolinic Acid Producibility of KefA-Deficient Strain

To compare quinolinic acid producibility of the kefA-deficient strain, W3110-ΔnadCΔkefA and MG1655-ΔnadCΔkefA strains of Example 1-4 were each transformed through a CaCl$_2$ method using the pPro-nadB_pCJ1-nadA plasmid. The transformed strains were each smeared on a LB-Km plating medium (10 g/L of yeast extract, 5 g/L of NaCl, 10 g/L of tryptone, 1.5% of agar, and 50 ug/L of kanamycin), and then, incubated at 37° C. overnight. Afterwards, a single kanamycin-resistant colony was collected, inoculated in 25 mL of quinolinic acid titer medium (see Table 1) by 1 platinum loop, and then, incubated with 250 rpm at 33° C. for 24 to 72 hours.

The quinolinic acid in the culture broth was analyzed by HPLC, and the results are shown in Table 3 below. As shown in Table 3, the concentration of the quinolinic acid was increased in the kefA-deficient strain, compared to a control strain. In particular, it was confirmed that the concentration of the quinolinic acid increased by at least 15% upon the deletion of kefA in the wild-type strain.

TABLE 3

| Strain | Plasmid | Quinolinic acid (g/L) |
| --- | --- | --- |
| W3110-ΔnadC | pPro-nadB_pCJ1-nadA | 3.6 |
| W3110-ΔnadCΔkefA | | 4.2 |
| MG1655-ΔnadC | | 2.2 |
| MG1655-ΔnadCΔkefA | | 2.7 |

2-3. Confirmation of Effects of Attenuated Activity of KefA (1) Preparation of Plasmid Substituting Start Codon of KefA To confirm weakening effects of KefA in strains producing quinolinic acid, the plasmid having weakened kefA was prepared. The nucleotide sequence of the gene of SEQ ID NO: 10 (NCBI Registration No. "GI::89107872") obtained from the NIH GenBank was used as the gene sequence. The ORF region of the kefA gene was amplified by modifying the start codon of the kefA from ATG to TTG, and primers of SEQ ID NOs: 32 and 33 having the recognition sites of restriction enzymes blunt and BamHI were synthesized. In addition, a self-promoter region of the kefA gene was amplified, and primers of SEQ ID NOs: 34 and 35 having the recognition sites of restriction enzymes SacI and blunt were synthesized.

PCR was performed using chromosomal DNA of *E. coli* K12 W3110 strain (ATCC No. 23257) as a template and oligonucleotides of SEQ ID NOs: 32 and 33 as primers. PfuUltra™ DNA polymerase (Stratagene) was used as a polymerase, and PCR was performed by repeating the cycle 30 times including denaturation at 96° C. for 30 seconds, annealing at 50° C. for 30 seconds, and extension at 72° C. for 30 seconds. Through PCR procedures, the amplified gene of about 0.15 kb, which contains the ORF region of the kefA and the recognition site of restriction enzyme BamHI, was obtained.

In addition, PCR was performed using chromosomal DNA of K12 W3110 as a template and oligonucleotides of SEQ ID NOs: 34 and 35 as primers. PfuUltra™ DNA polymerase (Stratagene) was used as a polymerase, and PCR was performed by repeating the cycle 30 times including denaturation at 96° C. for 30 seconds, annealing at 50° C. for 30 seconds, and extension at 72° C. for 30 seconds. Through PCR procedures, the amplified pKefA promoter of about 0.15 kb, which contains a self-promoter region of the kefA and the recognition site of restriction enzyme SacII, was obtained.

The ORF region of the kefA and the pKefA promoter that were obtained through PCR procedures were recovered through agarose gel elution, and then, were each treated with restriction enzymes BamHI and SacI. Afterwards, the ORF region of the kefA and the pKefA promoter were subjected to ligation into a pSG76C vector treated with restriction enzymes BamHI and SacI (J. Bacteriol. 179 (13), 4426-4428 (1997), NCBI genebank Y09892).

Accordingly, the vector having the self-promoter and the ORF region of the kefA, of which the start codon ATG was substituted with TTG, was prepared, and then, was named a pSG76C_kefA*(ATG→TTG) vector.

(2) Preparation of Strain Having Substituted Start Codon of kefA and Evaluation of Producibility of Quinolinic Acid E. coli W3110-ΔNadC was transformed with the pSG76C_kefA*(ATG→TTG) vector of Example 2-3(1) by means of electroporation, and then, the strain was smeared on a LB plating medium (10 g/L of tryptone, 5 g/L of yeast extract, 10 g/L of NaCl, and 1.5% of agar) containing chloramphenicol as a selective marker and incubated at a temperature of 37° C. overnight, to thereby select a strain showing a resistance against chloramphenicol. The selected strain as the template was directly subjected to PCR using primers of SEQ ID NOs: 33 and 34 under the same conditions, and then, the PCR products having a size of 0.30 kb were obtained from the 1.0% agarose gel. By performing a sequencing process, a strain, of which the start codon ATG of the kefA was substituted with TTG, was finally selected. The finally selected strain was then named W3110-ΔnadC_kefA*(ATG→TTG).

In addition, MG1655-ΔnadC was transformed with the pSG76C_kefA*(ATG→TTG) vector under the same conditions, and then, the substitution of the start codon of the kefA was confirmed. The strain obtained therefrom was named MG1655-ΔnadC_kefA*(ATG→TTG).

To compare quinolinic acid producibility of each of the transformed strains, a single chloramphenicol-resistant colony was collected from the strains of Table 4 below, inoculated in 25 mL of quinolinic acid titer medium (see Table 1) by 1 platinum loop, and then, incubated with 250 rpm at 33° C. for 24 to 72 hours. The quinolinic acid in the culture broth was analyzed by HPLC, and the results are shown in Table 4 below. Consequently, the strain having weakened kefA, i.e., the strain having the substituted start codon of the kefA, produced quinolinic acid at a concentration level that increased by 10%, compared to the control group.

TABLE 4

| Strain | Plasmid | Quinolinic acid (g/L) |
|---|---|---|
| W3110-ΔnadC | pPro-nadB_pCJ1-nadA | 3.5 |
| W3110-ΔnadC_kefA*(ATG->TTG) | | 4.0 |
| MG1655-ΔnadC | | 2.1 |

TABLE 4-continued

| Strain | Plasmid | Quinolinic acid (g/L) |
|---|---|---|
| MG1655-ΔnadC_kefA*(ATG->TTG) | | 2.5 |

Example 3. Evaluation of Sensitivity to Quinolinic Acid of kefA-Deficient Strain or kefA-Enhanced Strain 3.1 Evaluation of Sensitivity to Quinolinic Acid of Strains Producing Quinolinic Acid Based on the results of the evaluation of the quinolinic acid producibility above, it was expected that removal or elimination of the KefA would weaken re-entrance of external quinolinic acid into cells, thereby increasing the producibility of quinolinic acid. Based on such expectation, the kefA-deficient strain and kefA-enhanced strain were subjected to evaluation of sensitivity to quinolinic acid.

First, to attenuate growth and development in the production strains, it was confirmed whether the addition of 13 g/L of quinolinic acid, in which KOH was titrated to a 7.0 pH, had influence or not. That is, a single colony of the strain producing quinolinic acid was inoculated in 25 mL of a LB+1% glucose broth (10 g/L of yeast extract, 5 g/L of NaCl, 10 g/L of tryptone, 50 ug/L of kanamycin, and 10 g/L of glucose) by 1 platinum loop, and then, incubated with 250 rpm at 33° C. for 16 to 24 hours. Then, the OD600, the glucose consumption, and the residual quinolinic acid of the strain were measured.

TABLE 5

| Base strain | Plasmid | Medium condition | OD600 | Glucose consumption (g/L) | Residual quinolinic acid (g/L) |
|---|---|---|---|---|---|
| W3110-ΔnadC | pPro-nadB_pCJ1-nadA | 0 g/L of quinolinic acid | 9.1 | 10.0 | 0.1 |
| MG1655-ΔnadC | | | 8.3 | 9.0 | 0 |
| W3110-ΔnadC | | 13 g/L of quinolinic acid | 4.9 | 6.0 | 11.9 |
| MG1655-ΔnadC | | | 4.5 | 6.0 | 11.8 |

As shown in Table 5 above, when quinolinic acid was additionally added to the medium, it was confirmed that quinolinic acid was introduced into cells, thereby decreasing the growth and development and glucose-consumption speed to 40%.

In this regard, the manipulated pPro-nadB_pCJ1-nadA plasmid-introducing W3110ΔnadCΔkefA strain, in which the nadC was deleted and nadBA was enhanced, was deposited under the Budapest Treaty at the Korean Culture Center of Microorganisms (KCCM) on Nov. 7, 2013, with Accession No. KCCM11470P.

3.2 Evaluation of Sensitivity to Quinolinic Acid of KefA-Deficient Strain and KefA-Enhanced Strain (1) Preparation of Overexpression Vector of KefA Protein To prepare a vector able to overexpress the kefA gene derived from E. coli, chromosomal DNA E. coli K12 W3110 strain (ATCC No 23257) was used as a template. In addition, the nucleotide sequence of the gene of SEQ ID NO: 10 (NCBI Registration No. "GI::89107872") obtained from the NIH GenBank was used as the gene sequence. The ORF region of the kefA gene was amplified, and primers of SEQ ID NOs: 36 and 37 having the recognition sites of restriction enzymes EcoRV and HindIII were synthesized.

PCR was performed using chromosomal DNA of *E. coli* K12 W3110 strain as a template and oligonucleotides of SEQ ID NOs: 36 and 37 as primers. PfuUltra™ DNA polymerase (Stratagene) was used as a polymerase, and PCR was performed by repeating the cycle 30 times including denaturation at 96° C. for 30 seconds, annealing at 50° C. for 30 seconds, and extension at 72° C. for 2 minutes. Through PCR procedures, the amplified gene of about 3.3 kb, which contains the ORF region of the kefA gene and the recognition sites of restriction enzymes EcoRV and HindIII, was obtained.

The kefA gene obtained through PCR procedures was recovered through agarose gel elution, and then, was treated with restriction enzymes EcoRV and HindIII. Afterwards, the kefA gene was subjected to ligation into a pCL1920_pRhtB vector treated with restriction enzymes EcoRV and HindIII, leading to the expression of the kefA gene linked to a pRhtB promoter. The vector prepared therefrom was named a pCL_pRhtB-kefA vector.

(2) Evaluation of Sensitivity to Quinolinic Acid of KefA-Deficient Strain and KefA-Enhanced Strain To figure out whether the KefA membrane protein influenced the introduction of quinolinic acid, under the same method as Example 2-4(1), the kefA gene-deficient strain and the kefA gene-enhanced strain were subjected to evaluation of sensitivity to quinolinic acid.

TABLE 6

| Base strain | Plasmid | Medium condition | OD600 | Glucose consumption (g/L) | Residual quinolinic acid (g/L) |
| --- | --- | --- | --- | --- | --- |
| W3110-ΔnadC | pPro-nadB_pCJ1-nadA pCL1920 | 0 g/L quinolinic acid | 10.2 | 10.0 | 0.2 |
| W3110-ΔnadC | pPro-nadB_pCJ1-nadA pCL_PrhtB-kefA | | 5.2 | 6.2 | 0 |
| W3110-ΔnadCΔkefA | pPro-nadB_pCJ1-nadA pCL1920 | | 10.5 | 10.0 | 0.2 |
| W3110-ΔnadC | pPro-nadB_pCJ1-nadA pCL1920 | 13 g/L quinolinic acid | 5.0 | 6.2 | 12.0 |
| W3110-ΔnadC | pPro-nadB_pCJ1-nadA pCL_PrhtB-kefA | | 2.1 | 3.2 | 11.5 |
| W3110-ΔnadCΔkefA | pPro-nadB_pCJ1-nadA pCL1920 | | 8.2 | 8.0 | 12.5 |

As shown in Table 6 above, when the kefA gene was also enhanced in the LB broth, the growth and development and the glucose consumption speed of the strains producing quinolinic acid significantly decreased to about 40%, compared to the control strain in which the nadBA gene was enhanced in W3110-ΔnadC. It was also confirmed that the production of quinolinic acid was not found at all. In addition, under the condition where quinolinic acid was additionally added to the medium, the growth and development and glucose consumption speed of the kefA-deficient strain improved up to 110%, compared to those of the control strain, whereas the growth and development and glucose consumption speed of the kefA-enhanced strain decreased to 50%, compared to those of the control strain.

Based on the results above, it was determined that the KefA membrane protein was involved in the introduction of quinolinic acid into cells. In addition, it was confirmed that the removal or elimination of the kefA may attenuate sensitivity to quinolinic acid of the strain producing quinolinic acid, and furthermore, may lead to increased production of quinolinic acid.

Name of depository authority: Korean Culture Center of Microorganisms (International)
Accession number: KCCM11470P
Deposit date: Nov. 7, 2013

The invention claimed is:

1. A recombinant microorganism of the genus *Escherichia* producing quinolinic acid, wherein the activity of a protein having the amino acid sequence of SEQ ID NO: 1 is attenuated or eliminated, and the activity of quinolinate phosphoribosyltransferase is attenuated or eliminated, wherein the recombinant microorganism is *Escherichia coli*.

2. The recombinant microorganism according to claim 1, wherein the activity of at least one enzyme selected from the group consisting of L-aspartate oxidase and quinolinate synthase is further enhanced compared to a microorganism that is not modified to the enhancement of the activity of the at least one enzyme.

3. The recombinant microorganism according to claim 1, wherein the quinolinate phosphoribosyltransferase has the amino acid sequence of SEQ ID NO: 29.

4. The recombinant microorganism according to claim 2, wherein the L-aspartate oxidase has the amino acid sequence of SEQ ID NO: 30, and the quinolinate synthase has the amino acid sequence of SEQ ID NO: 31.

5. A method of producing quinolinic acid, the method comprising:
   culturing the recombinant microorganism of claim 1 in a medium; and
   recovering quinolinic acid from the medium or the microorganism.

* * * * *